(12) United States Patent
Chaubet et al.

(10) Patent No.: US 6,362,396 B1
(45) Date of Patent: Mar. 26, 2002

(54) CHIMERIC GENE FOR THE TRANSFORMATION OF PLANTS

(75) Inventors: Nicole Chaubet; Claude Gigot, both of Strasbourg; Georges Freyssinet, St Cyr au Mont d'Or, all of (FR); Bernard Leroux, Raleigh, NC (US); Michel Lebrun, Montpellier; Alain Sailland, Lyons, both of (FR)

(73) Assignee: Aventis Crop Science, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/013,520

(22) Filed: Jan. 26, 1998

Related U.S. Application Data

(63) Continuation of application No. 08/475,189, filed on Jun. 7, 1995, now Pat. No. 5,792,930, which is a continuation of application No. 08/239,947, filed on May 9, 1994, now Pat. No. 5,491,288, which is a continuation of application No. 07/847,597, filed on May 5, 1992, now abandoned.

(51) Int. Cl.[7] .......................... A01H 5/00; A01H 4/00; C12N 5/04

(52) U.S. Cl. ...................... 800/295; 800/290; 536/23.6; 536/24.1; 435/69.1

(58) Field of Search .................................. 800/295, 298; 536/23.6, 24.1, 23.2, 23.1; 435/69.1, 69.7

(56) References Cited

U.S. PATENT DOCUMENTS

| 4,940,835 A | | 7/1990 | Shah et al. | |
|---|---|---|---|---|
| 5,491,288 A | * | 2/1996 | Chaubet et al. | ............. 800/205 |
| 5,510,471 A | * | 4/1996 | LeBrun et al. | |
| 5,633,448 A | | 5/1997 | LeBrun et al. | |
| 5,776,760 A | | 7/1998 | Barry et al. | |
| 5,792,930 A | * | 8/1998 | Chaubet et al. | ............. 800/205 |

OTHER PUBLICATIONS

Wasmann et al., Mol. Gen. Genet. 205: 446–453, 1986*
Comai et al., J. Biol Chem. 263: 15104–15109, 1989.*
Wasmann, Mol. Gen. Genet. 205:446 (1986).
Smeekens, TIBS 15:73 (1990).
Comai, J. Biol. Chem. 263:15104 (1988).
Keegsta, Ann. Rev. Plant. Physiol. Plant Mol. Biol. 40:471 (1989).

* cited by examiner

Primary Examiner—Gary Benzion
(74) Attorney, Agent, or Firm—Connolly Bove Lodge & Hutz LLP

(57) ABSTRACT

1) Chimeric gone for conferring to plants an increased tolerance to a herbicide. 2) It comprises, in the direction of transcription, a promoter region, a transit peptide region, a sequence encoding glyphosate tolerance and a polyadenylation signal region, wherein the promoter region consists of at least one promoter of a plant histone gene enabling the expression of the herbicide tolerance protein in the regions of glyphosate accumulation. 3) Production of glyphosate-tolerant plants.

5 Claims, No Drawings

CHIMERIC GENE FOR THE TRANSFORMATION OF PLANTS

This application is a continuation of U.S. Ser. No. 08/475,189, filed Jun. 7, 1995. Now U.S. Pat. No. 5,792,930 which is a continuation of U.S. Ser. No. 08/239,947, filed on May 9, 1994, now U.S. Pat. No. 5,491,288, which is a file wrapper continuation of U.S. Ser. No. 07/847,597, filed May 5, 1992, now abandoned.

The present invention relates to novel promoters, to novel chimeric genes containing them and to their use in plants for conferring to them an increased tolerance to herbicides. It also relates to the plant cells transformed by means of these genes and to the transformed plants regenerated from these cells as well as to the plants derived from crossbreedings using these transformed plants.

Glyphosate, sulfosate or fosametine are broad-spectrum systemic herbicides of the phosphonomethyl-glycine family. They act essentially as competitive inhibitors of 5-(enolpyruvyl)shikimate-3-phosphate synthase (EC 2.5.1.19) or EPSPS in relation to PEP (phosphoenolpyruvate). After their application to the plant, they are translocated inside the plant where they accumulate in the rapidly growing parts, in particular the caulinary and root apexes, causing the deterioration and even the destruction of sensitive plants.

Plastidial EPSPS, the main target of these products, is an enzyme of the aromatic amino acid biosynthesis pathway which is encoded by one or more nuclear genes and synthesised in the form of a cytoplasmic precursor and then imported into the plastids where it accumulates in its natural form.

The tolerance of plants to glyphosate and to products of the family is obtained by the stable introduction inside their genome of an EPSPS gene of plant or bacterial origin mutant or nonmutant with respect to the characteristics of the inhibition of the product of this gene by glyphosate. Given the mode of action of glyphosate, it is useful to be able to express the product of translation of this gene so as to permit its substantial accumulation in plastids.

It is known, for example from American U.S. Pat. No. 4,535,060, to confer to a plant a tolerance to a herbicide of the abovementioned type, in particular N-(phosphonomethyl)glycine or glyphosate, by introducing into the plant genome a gene encoding an EPSPS carrying at least one mutation making this enzyme more resistant to its competitive inhibitor (glyphosate), after localisation of the enzyme in the plastidial compartment. However, these techniques need to be improved in order to achieve greater reliability in the use of these plants under agronomic conditions.

In the present description, "plant" is understood as meaning any differentiated multicellular organism capable of photosynthesis and "plant cell" any cell derived from a plant and capable of forming undifferentiated tissues such as calluses or differentiated tissues such as embryos or plant sections, plants or seeds.

The subject of the present invention is the production of transformed plants having an increased tolerance to herbicides in general and particularly of the phosphonomethylglycine family by regenerating cells transformed by means of novel chimeric genes comprising a gene for tolerance of these herbicides. The invention also relates to novel chimeric genes as well as to transformed plants which are more tolerant due to better tolerance of the rapidly growing parts, as well as to plants derived from crossbreedings using these transformed plants. The subject of the invention is also novel promoters for constructing the above chimeric genes and comprising a DNA sequence capable of serving as promoter region in a chimeric gene which may be used for transforming plants, which comprises, in the direction of transcription, at least one promoter or a fragment thereof of a plant histone gene enabling the expression of the herbicide tolerance protein in the regions of accumulation of said herbicide.

More particularly, the subject of the invention is a chimeric gene for conferring to plants an increased tolerance to a herbicide whose target is EPSPS, comprising, in the direction of transcription, a promoter region, a transit peptide region, a sequence encoding a glyphosate tolerance enzyme and a polyadenylation signal region, wherein the promoter region consists of at least one fragment of a plant histone gene promoter enabling the preferential expression of a herbicide tolerance protein in the regions of glyphosate accumulation.

The histone gene is derived from a monocotyledonous plant such as for example wheat, maize or rice, or preferably from a dicotyledonous plant such as for example lucerne, sunflower, soya bean, colza or preferably *Arabidopsis thaliana*.CF Plant Mol. Biol Vol 8, 1987, p 179–191 Chaboute et al.

A histone gene of the H3 or preferably H4 type is preferably used, alone or under a multiplicated especially duplicated, form.

The promoter region of the chimeric gene according to the invention may in addition advantageously comprise at least one fragment of a promoter from a gene which is expressed naturally in plants, that is to say, for example, a promoter of viral origin such as the 35S RNA promoter of the cauliflower mosaic virus (CaMv35S), or of plant origin such as the small subunit of the ribulose 1,5-diphosphate carboxylase oxygenase (RuBisCO) gene from a crop such as for example maize or sunflower.

The transit peptide region comprises, in the direction of transcription, at least one transit peptide of a plant gene encoding a plastid-localised enzyme, a partial sequence of the N-terminal mature part of a plant gene encoding a plastid-localised enzyme and then a second transit peptide of a plant gene encoding a plastid-localised enzyme, preferably the RuBisCO gene.

The above transit peptides which can be used in the transit peptide region may be known per se and may be of plant origin, for example, derived from maize, sunflower, peas, tobacco or the like. The first and the second transit peptides may be identical, analogous or different. They may in addition each comprise one or more transit peptide units.

The partial sequence of the N-terminal mature part is derived from a plant gene encoding a plastid-localised enzyme, such as for example a maize, sunflower or pea gene or the like, it being possible for the original plant species to be identical, analogous or different from that from which the first and second transit peptides are derived respectively. Furthermore, the partial sequence of the mature part may comprise a varying number of amino acids, generally from 15 to 40, preferably from 18 to 33.

Construction of the entire transit peptide region may be known per se, in particular by fusion or any other suitable means. The role of this characteristic region is to enable the release of a mature protein with a maximum efficiency, preferably in native form.

The coding sequence for herbicide tolerance which may be used in the chimeric gene according to the invention encodes a mutant EPSPS having a degree of glyphosate tolerance. This sequence, obtained in particular by mutation of the EPSPS gene, may be of bacterial origin, for example derived from *Salmonella typhymurium* (and called in the text which follows "AroA gene"), or of plant origin, for example from petunia or from tomatoes. This sequence may comprise one or more mutations, for example the Pro 101 to Ser mutation or alternatively the Gly 96 to Ala mutations. The untranslated polyadenylation signal region in 3' of the chimeric gene according to the invention may be of any origin, for example bacterial, such as the nopaline synthase is gene, or of plant origin, such as the small subunit of the maize or sunflower RuBisCO.

The chimeric gene according to the invention may comprise, in addition to the above essential parts, an untranslated intermediate region (linker) between the promoter region and the coding sequence which may be of any origin, bacterial, viral or plant.

EXAMPLE 1
CONSTRUCTION OF A CHIMERIC GENE

The construction of a chimeric gene according to the invention is carried out using the elements:

1) Promoter: the promoter is isolated from an H4 A777 histone clone and a H4 A748 histone clone respectively, from *Arabidopsis thaliana*, Strasbourg strain, which are described by Chaboute (thesis from the University of Strasbourg, 1987) and PLANT MOL.BIOL. Vol 8, 1987 p 179–191. These promoters, comprising about 1 kpb between the XhoI sites used for its isolation, are used as they are or in duplicate form or fused with a single or double CaMV35S promoter, that is to say part of which has been duplicated.

2) Transfer region: the two transit peptides as well as the mature protein elements used are derived from the cloned cDNA of the small subunit of maize RuBisCO corresponding to the gene described by Lebrun et al. Nucl. Acids Res. 15:4360 (1987) and from the cloned cDNA of the small subunit of sunflower RuBisCO isolated by Waksman et al. Nucl. Acids Res. 15:1328 (1987). More specifically, the transfer region comprises, in the direction of translation:

a transit peptide of the small subunit of sunflower RuBisCO, a sequence of 22 amino acids of the N-terminal mature part of the small subunit of maize RuBisCO, a transit peptide of the small subunit of maize RuBisCO.

Other similar genes may contain sequences of 10 to 40 and preferably 18 and 33 amino acids respectively.

In order to provide a comparative element, another construction was carried out containing, in the direction of transcription, "double CaMV35S promoter/ transit peptide of the SSU of the sunflower RuBisCO/N-terminal sequence of 22 amino acids of the SSU of maize RuBisCO/transit peptide of the SSU of maize RuBisCO/AroA gene/nos" (pRPA-BL 410).

3) Structural gene: it is derived from the mutant (Pro 101 to Ser) EPSPS gene of *Salmonella typhymurium* isolated by Stalker et al. J. Biol. Chem. 260:4724 (1985). The pMG34-2 clone (provided by Calgene) was linearized with XbaI and then treated with *Vigna radiata* nuclease. After recutting with SmaI, the two blunt ends were ligated. The clone obtained possesses an NcoI site in the initiator ATG as well as a 17-bp SalI site downstream of the stop codon. This clone was called pRPA-BL 104.

4) Polyadenylation signal region: the fragment is derived from the nopaline synthase gene of pTi37 (Bevan et al. Nature 304:187 , 1983). This site is contained in a 260-bp MboI fragment (Fraley et al., 1983; Patent Application PCT 84/02913) which was treated with Klenow polymerase and cloned in the SmaI site of M13 mp 18 in order to introduce the BamHI and EcoRI sites at the 5' and 3' ends respectively.

After cutting with BamHI and treating with *Vigna radiata* nuclease followed by cutting with EcoRI and treating with Klenow polymerase, the resulting fragment was introduced in the vector p-BL 20 (cf. French Patent Application 88/04130), cut by XbaI and BamHI and treated with Klenow polymerase. After recutting with SalI and SstI, a fragment of about 0.4 kbp containing the 3' nos sequence on the side of the SalI site and the right end on the T-DNA side of the SstI site is obtained.

The assembly of all these elements was carried out in the following manner:

"Transit peptide of the SSU of the maize RuBisCO/AroA gene" fusion:

The transit peptide of the SSU of the maize RuBisCO gene is derived from a 192-bp EcoRI-SphI fragment obtained from the cDNA corresponding to the SSU gene of the maize RuBisCO gene, described by Lebrun et al. (1987), possessing an NcoI site spanning the initiation codon for translation and an SphI site corresponding to the cleavage site of the transit peptide.

Translational fusion is obtained between the maize transit peptide and the bacterial EPSPS gene by treating the SphI end with bacteriophage T4 polymerase and by ligating it with the Klenow polymerase-treated NcoI end of the AroA gene from pRPA-BL 104, recut with EcoRI.

Transit peptide of the SSU of maize RuBisCO/sequence of 22 amino acids of the mature part of the maize gene/AroA gene fusion:

Similarly, a 228-bp EcoRI-HindII fragment of the cDNA of the SSU of the maize RuBisCO gene is ligated with the Klenow polymerase-treated NcoI end of the AroA gene from pRPA-BL 104 and recut with EcoRI. A translational fusion is obtained between the transit peptide of the SSU of maize RuBisCO, the 22 amino acids of the mature part of the SSU of maize RuBisCO and the bacterial EPSPS gene.

Transit peptide of the SSU of sunflower RuBisCO:

The fragment is derived from the cDNA isolated by Waksman and Freyssinet Nucl. Acids Res. 15:1328 (1987). An SphI site was created at the cleavage site of the transit peptide according to the method of Zoller and Smith Methods in Enzymology 154:329 (1984). The transit peptide of the SSU of sunflower RuBisCO thus obtained is a 171-bp EcorI-SphI fragment.

Transit peptide of the SSU of sunflower RuBisCO/ sequence of 22 amino acids of the mature part of the SSU of maize RuBisCO/AroA gene fusion:

The construct containing the transit peptide of the SSU of maize RuBisCO/sequence of 22 amino acids of the SSU of maize RuBisCO was cut with EcoRI-SphI and then ligated with the 171-bp EcoRI-SphI fragment corresponding to the transit peptide of the SSU of sunflower RuBisCO. A resulting construct exhibits a substitution of the EcoRI-SphI fragments and is a translational fusion "transit peptide of the SSU of sunflower RuBisCO/sequence of 22 amino acids of the SSU of maize RuBisCO/AroA gene.

The EcoRI-SalI fragment was ligated with the SalI-SstI fragment containing the 3' nos sequence and the right end of the T-DNA. The resulting EcoRI-SstI fragment, comprising "transit peptide of the SSU of sunflower RuBisCO/sequence of 22 amino acids of the SSU of maize RuBisCO/AroA gene/3' nos/T-DNA right end", is substituted for the EcoRI-SstI fragment containing the right end of the T-DNA of the plasmid 150 A alpha 2 containing the double CaMV promoter. The transcriptional fusion "double CaMV/transit peptide of the SSU of sunflower RuBisCO/sequence of 22 amino acids of the SSU of maize RuBisCO/AroA gene/3' nosy" in the vector 150 A alpha 2 was called pRPA-BL 294.

"Transit peptide of the SSU of sunflower RuBisCO/ sequence of 22 amino acids of the SSU of maize RuBisCO/ transit peptide of the SSU of maize RuBisCO/AroA gene" fusion:

The above construct is cut with NcoI-HindIII, releasing the AroA gene. Next it is ligated with a 1.5 kbp NcoI-HindIII fragment containing the "transit peptide of the SSU of maize RuBisCO/AroA gene" fusion. A resulting construct exhibits a substitution of the NcoI-HindIII fragments and is a translational fusion "transit peptide of the SSU of sunflower RuBisCO/sequence of 22 amino acids of SSU of maize RuBisCO/transit peptide of the SSU of maize RuBisCO/AroA gene".

The EcoRI-SalI fragment was ligated with the SalI- SstI fragment containing the 3' nos sequence and the right end of the T-DNA. The resulting EcoRI-SstI fragment comprising "transit peptide of the SSU of sunflower RuBisCO/sequence of 22 amino acids of the SSU of maize RuBisCO/transit peptide of the SSU of maize RuBisCO/AroA gene/3' nos/ T-DNA right end" is substituted for the EcoRI-SstI fragment containing the right end of the T-DNA of the plasmid 150 A alpha 2 containing the double CaMV promoter. The transcriptional fusion "double CaMV/transit peptide of the SSU of sunflower RuBisCO/sequence of 22 amino acids of the SSU of maize RuBisCO/transit peptide of the SSU of maize RuBisCO/AroA gene/3' nos" in the vector 150 A alpha 2 was called pRPA-BL 410.

All the constructs were obtained by substituting the double CaMV promoter region of the pRPA-BL 410 construct obtained above, which is cut in EcoRI-HindIII, with a HindIII-EcoRI fragment containing the various promoter elements which follow:

A) Single H4 A748 histone promoter:

An XhoI-XhoI fragment of about 1 kbp containing the *Arabidopsis thaliana* H4 748 histone promoter (Plant Mol- .Biol. Vol 8, 1987 p 179–191) Bwas ligated with SalI-cut pUC 19. This clone was then cut with XbaI treated with Klenow polymerase and EcoRI treated with Klenow polymerase and then ligated under conditions which promote recircularisation. The HindIII-EcoRI fragment containing the histone promoter was substituted for the HindIII-EcoRI fragment containing the pRPA-BL 410 double CaMV promoter.

The resulting clone contains the "H4 histone promoter/ transit peptide of the SSU of sunflower RuBisCO/sequence of 22 amino acids of the SSU of maize RuBisCO/transit peptide of the SSU of maize RuBisCO/AroA gene/nos" and was called pRPA-BL 498.

B) Single H4 777 histone promoter

An XhoI fragment of about 1 kbp containing all the proximal 5' regions of the *Arabidolpsis thaliana* H4 777 histone gene cf Plant Mol. Biol. Vol 8, 1987 p 179–191 was cloned at the SalI site of the plasmid pUC 19 with an orientation such that the sites of the pUC 19 polylinker from XbaI to EcoRI were situated downstream of the site of initiation of transcription.

Transit region of the SSU of sunflower RuBisCO/AroA fusion An EcoRI-HindII fragment of the cDNA of the SSU of sunflower RuBisCO isolated by Waksman and Freyssinet (1987) encoding the transit peptide and 30 amino acids of the mature protein was cloned at the EcoRI and SmaI sites of pUC 18.

An EcoRI-XbaI fragment was isolated and inserted upstream of the AroA gene of pMG 34-2 (provided by Calgene) at the EcoRI and XbaI sites. In order to put the 2 coding regions in frame, the EcoR-HindIII insert of this clone was inserted in M13 mp19 at the EcoRI and HindIII sites.

The replicative form of the DNA of this clone was linearised with XbaI and then treated with *Vigna radiata* nuclease. After ligation under conditions promoting recircularisation and transformation, the DNA of some clones was analysed by sequencing. One of the clones obtained produces a translational fusion between the SSU element of RuBisCO and the AroA fragment, the initiation codon ATG of the latter being lost. The sequence of the junction between these two elements is as follows:

GAC GGGGATCCGGAA

SSU linker AroA.

This fusion therefore comprises in the direction of translation: transit peptide of the SSU of sunflower RuBisCO/30 amino acids of the mature part of the SSU of sunflower RuBisCO/3 amino acids corresponding to the intermediate linker/AroA.

Construction of pRPA - BL - 240

The plasmid comprising the promoter of the H4 777 histone gene described above was cut with XbaI, treated with Klenow polymerase and the fragment resulting from the HindIII recut isolated. The plasmid containing the sunflower transit peptide/AroA fusion described above was cut with EcoRI, treated with Klenow polymerase and the fragment resulting from the HindIII recut isolated. These two fragments were ligated in the presence of HindIII-cut pUC 19. One of the resulting clones has the following structure: histone promoter/region encoding the transit peptide of the SSU of sunflower RuBisCO/zone encoding 30 amino acids of the mature part of the SSU of sunflower RuBisCO/zone encoding 3 amino acids corresponding to the intermediate linker/zone encoding AroA.

This clone was cut with SalI, treated with Klenow polymerase and then, after recutting with HindIII, the isolated fragment was ligated with the plasmid containing the polyadenylation region, cut with BamHI, treated with Klenow polymerase and then recut with HindIII.

One of the resulting clones has the following structure: histone promoter/zone encoding the transit peptide of the SSU of sunflower RuBisCO/zone encoding 30 amino acids of the mature part of sunflower RuBisCO/zone encoding 3 amino acids corresponding to the intermediate linker/zone encoding AroA/3' nos.

The above plasmid was linearized with HindIII and inserted at the unique HindIII site of the vector pRPA-BL 127 constructed in the following manner: the vector pCGN 1152 possessing a hygromycin-resistant gene under the control of the mannopine synthase gene and the terminator of the Tm1 gene (provided by Calgene) was digested with HindIII and religated to itself, leading to the creation of a unique HindIII cloning site.

One of the resulting clones comprises the following transcriptional fusion, from the left end of the T-DNA of the plasmid pRPA-BL 127: histone promoter/transit zone of the SSU of sunflower RuBisCO/AroA/3' nos, and was called pRPA-BL-240.

C) Duplication of the histone promoter (=double histone promoter).

The H4 histone promoter in pUC 19 described above was digested with NdeI, treated with Klenow polymerase and then recut with HindIII. The fragment removed was substituted by a HindIII—EcoRV fragment purified by digesting the plasmid carrying the H4 histone promoter. One of the clones obtained has the following structure: 5' region of the H4 promoter of 530 bp from HindIII to NdeI, duplicated region corresponding to the two directly repeated fragments of 330 bp from NdeI to EcoRV, 3' region of the H4 promoter of 140 bp from EcoRV to EcoRI.

The HindIII-EcoRI fragment containing the double histone promoter was substituted for the HindIII-EcoRI fragment containing the double CaMV of pRPA-BL 410. The resulting clone contains a "double histone promoter/transit peptide of the SSU of sunflower RuBisCO/sequence of 22 amino acids of the SSU of maize RuBisCO/maize transit peptide/AroA gene/nos" and was called pRPA-BL 488.

D) Hybrid double CaMV/histone promoter:

The H4 A748 histone promoter, in the HindIII-EcoRI cassette described above (single H4 A748 histone promoter), is cut with AccI, treated with Klenow polymerase and then cut with EcoRI. The resulting fragment of 580 bp is ligated with the double CaMV promoter which is cut with EcoRV-EcoRI. The resulting clone comprising the double CaMV 3' part of the histone promoter fusion is cut with HindIII-EcoRI and substituted for the HindIII-EcoRI fragment of pRPA-BL 410 comprising the double CaMV. The resulting construct comprises a "double CaMV promoter/3' part histone promoter/transit peptide of the SSU of sunflower RuBisCO/sequence of 22 amino acids of the SSU of maize RuBisCO/transit peptide of the SSU of maize RuBisCO/AroA gene/nos" and was called pRPA-BL 502.

EXAMPLE 2

RESISTANCE OF THE TRANSFORMED PLANTS

1. Transformation:

The vector is introduced into the nononcogenic agrobacterium strain EHA 101 (Hood et al., 1987) carrying the cosmid pTVK 291 (Komari et al., 1986). The transformation method is based on the procedure of Horsh et al. (1985).

2. Regeneration:

The regeneration of the tobacco PBD6 (source SEITA France) using foliar explants is carried out on a Murashige and Skoog (MS) basic medium containing 30 g/l of sucrose and 200 g/ml of kanamycin. The foliar explants are removed from greenhouse- or in vitro-grown plants and transformed according to the foliar disc method (Science 1985, Vol. 227, p. 1229–1231) in three successive stages: the first comprises the induction of shoots on an MS medium supplemented with 30 g of sucrose containing 0.05 mg of naphthylacetic acid (ANA) and 2 mg/l of benzylaminopurine (BAP), for 15 days. The shoots formed during this stage are then developed by culturing on an MS medium supplemented with 30 g/l of sucrose, but not containing hormone, for 10 days. The developed shoots are then removed and they are cultured on a half-diluted MS planting medium containing half the content of salts, vitamins and sugars and not containing hormone. After about 15 days, the deeply-rooted shoots are placed in soil. Untransformed tobacco PBD 6 plants are grown up to the same stage as controls.

3. Measurement of the glyphosate tolerance:

The best plants obtained from the regeneration of transformed tobaccos are selected under a greenhouse after treating the plants, at the 5-leaf stage, by spraying with an aqueous suspension of glyphosate at a dose corresponding to 0.6 kg/ha of active substance. The plants selected are self-fertilised and the seeds are sown on an MS medium supplemented with 30 g/l of sucrose and 200 micrograms/ml of kanamycin. The seeds obtained from plants having a segregation ratio of ¾ of resistant plants-¼ of sensitive plants were kept. Molecular hybridization analysis enabled the plants having integrated only one copy of the T-DNA to be determined. These plants were taken to the heterozygote or homozygote state by crossbreeding and selection. These plants were sown under natural conditions, in the open, and sprayed at the 5-leaf stage with a dose of 0.8 kg/ha of glyphosate (Round Up). The results correspond to the observation of phytotoxicity indices taken at the end of 30 days after the treatment. Under these conditions, it is observed that the plants transformed with the constructs exhibit an acceptable tolerance (pRPA-BL 240 and 410) or even a good tolerance (pRPA-BL 488 and 502) whereas the control plants are completely destroyed.

These results clearly show the improvement brought by the use of a chimeric gene according to the invention for the same gene encoding the glyphosate tolerance.

The transformed plants according to the invention may be used as parents for producing lines and hybrids having an increased tolerance to glyphosate.

EXAMPLE 3

Spring colzas, Westar cultivar, resistant to glyphosate, were obtained using the method of BOULTER et al., 1990 (Plant Science, 70: 91–99), with the constructs pRPA-BL 488 (dH-At-PTO-aroA-nos), pRPA-BL 502 (CaMV/H-At-PTO- aroA-nos). These plants were resistant to a greenhouse treatment with glyphosate at 400 g a.s/ha (grams of active substance per hectare, a treatment which destroys nontransgenic plants.

What is claimed is:

1. A plant cell containing a chimeric gene, the chimeric gene encoding a transit peptide region comprising, in the direction of translation, at least one transit peptide of a plastid-localized enzyme, a partial sequence of an N-terminal mature part of a plastid-localized enzyme, and a second transit peptide of a plastid-localized enzyme.

2. The plant cell of claim 1, wherein the transit peptides and partial mature sequence are from sunflower or maize.

3. The plant cell of claim 2, wherein the chimeric gene further comprises a promoter region comprising at least one fragment of an Arabidopsis H3 or H4 histone gene promoter.

4. A plant which contains in its genome a chimeric gene encoding a transit peptide region comprising, in the direction of translation, at least one transit peptide of a plant gene which encodes a plastid-localized enzyme, a partial sequence of an N-terminal mature part of the plastid-localized enzyme, and a second transit peptide of a plastid-localized enzyme.

5. The plant of claim 4, wherein the chimeric gene further comprises a promoter region comprising at least one fragment of an Arabidopsis H3 or H4 histone gene promoter.

* * * * *